US006146859A

United States Patent [19]
Chen et al.

[11] Patent Number: 6,146,859
[45] Date of Patent: Nov. 14, 2000

[54] FACILE SYNTHESIS OF L-HOMOPHENYLALANINE BY EQUILIBRIUM SHIFT ENZYMATIC REACTION USING ENGINEERED TYROSINE AMINOTRANSFERASE

[75] Inventors: Shui-Tein Chen, Taipei; Min-Jen Tseng, Kao-Xiung, both of Taiwan; Boonyaras Sookkheo, Surat-Thani, Thailand

[73] Assignee: Academia Sinica, Taipei, Taiwan

[21] Appl. No.: 09/384,667

[22] Filed: Aug. 27, 1999

[51] Int. Cl.⁷ .............................. C12P 13/22; C12P 13/04
[52] U.S. Cl. ............................................ 435/108; 435/106
[58] Field of Search ..................... 435/193, 106, 435/108

[56] References Cited

U.S. PATENT DOCUMENTS 4,525,454   6/1985   Rozzell et al. ........................... 435/106

FOREIGN PATENT DOCUMENTS 3112490   5/1991   Japan ............................... C12P 13/22
3112491   5/1991   Japan ............................... C12P 13/22

OTHER PUBLICATIONS

Senkpeil et al.. Abstr.pap.Am.Chem.Soc, 213 Meet., Pt. 1, BIOT198, Apr. 19, 1997.

Anthony J. Pearson et al., "A Formal Total Synthesis of the ACE Inhibitor K–13. An Application of Arrene–Ruthenium Chemistry to Complex Chemical Synthesis" J. Org. Chem. vol. 59 , 1994, pp. 2304–2313.

Tatsuro Kijima et al., "Facile Optical Resolution of Amino Acid Esters via Hydrolysis by an Industrial Enzyme in Organic Solvents" J. Chem. Tech. Biotechnol. vol. 59, 1994, pp. 61–65.

Miguel A. Ondetti, et al., "Inhibition of the Renin–Angiotensin System. A New Approach to the Therapy of Hypertension" J. Medicinal. Chem. vol. 24(4), 1981, pp. 355–361.

Shui–Tein Chen et al., "Kinetic Resolution of N–Protected Amino Acid Esters in Organic Solvents Catalyzed By A Stable Industrial Alkaline Protease" Biotechnol. Lett. vol. 13(11), 1991, pp. 773–778.

Ching–Shih Chen et al., "Quantitative Analyses of Biochemical Kinetic Resolution of Enantiomers" J. Am. Chem. Soc. vol. 104, 1982, pp. 7294–7298.

*Primary Examiner*—Rebecca E. Pronty
*Assistant Examiner*—Maryam Monshipouri
*Attorney, Agent, or Firm*—Cohen, Pontani, Lieberman & Pavane

[57] ABSTRACT

A process for producing L-homophenylalanine comprises the step of reacting 2-oxo-4-phenylbutyric acid with a L-amino acid in the presence of tyrosine aminotransferase in a reaction solution to produce L-homophenylalanine.

20 Claims, 4 Drawing Sheets

REAGENTS AND CONDITIONS: i. MeOHM, $H_2SO_4$(CAT);
ii. NaOMe, DIMETHYL OXALATE, THF;
iii. 7N HCl, REFLUX.

FACILE SYNTHESIS OF L-HOMOPHENYLALANINE BY EQUILIBRIUM SHIFT ENZYMATIC REACTION USING ENGINEERED TYROSINE AMINOTRANSFERASE

BACKGROUND OF THE INVENTION

1. Field of the Invention

The present invention relates to a method of producing L-homophenylalanine, an angiotensin-converting enzyme (ACE) inhibitor, by reacting a L-amino acid such as L-glutamic acid with 4-phenyl-2-oxobutanoic acid in the presence of tyrosine aminotransferase.

2. Description of the Related Art

L-homophenylalanine (L-4-phenyl-2-aminobutanoic acid) is a member of a new class of oral angiotensin-converting enzyme inhibitors, which has shown a great potential as an anti-hypertension drug. Chemical or chemoenzymatical synthesises of L-homophenylalanine have been reported in various references. See Richard et al., *J. Org. Chem* 1998, 63: 7875; Pearson et al., *J. Org. Chem.*, 1994, 59:2304; Richard et al., *J. Chem. Soc. Perkin Trans.*, *I*, 1998, 1903; Fraser et al., *Synlett*, 1994, 5:379; Kijima et al., *J. Chem. Tech. Biotechnol.*, 1994, 59:61; Ondetti et al., *J. Med. Chem.*, 1981, 24:355; Chen et al., *J. Am. Chem. Soc.*, 104:7294; Chen et al., *Biotechnol. Lett.*,1991, 13:773; Senuma et al., *Apply Biochem. Biotech.*, 1989, 22:141.

U.S. Pat. No. 4,525,454 discloses a process for producing L-homophenylalanine by reacting 4-phenyl-2-oxobutanoic acid with L-aspartic acid in the presence of transaminase enzyme, and then decarboxylating the oxaloacetate produced therefrom. However, the process requires aspartic-glutamic transaminase as catalytic enzyme, aspartic acid as a substrate. A coupled decarboxylation reaction is also required to obtain a complete conversion.

Senuma et al., *Apply Biochem. Biotech.*, 1989, 22:141. reported a method of converting L-2-oxo-phenylbutyric acid to L-homophenylalanine by a microbial aminotransferase. However, the report concludes that L-aspartic acid is a better substrate than L-glutamic acid because the former showed higher conversion yield than the latter. It was found that 2-oxo-4-phenylbutyric acid markedly inhibited the activity of the aminotransferase, which is not specified, and the conversion yield at more than 0.2M.

SUMMARY OF THE INVENTION

The present invention is directed to a novel process of aminotransferase-catalyzed synthesis of L-homophenylalanine. Particularly, genetically engineered tyrosine-aminotransferase (glutamic-aromatic aminotransferase) is used in this novel process to catalyze the conversion reaction in the presence of a high concentration of the substrates. The genetically engineered tyrosine-aminotransferase has a broad substrate specificity so that a variety of amino acids including glutamic acid can be used as amino donors in the reaction. Since glutamic acid costs less than other amino acids, it is economically feasible to use it as the amino donor in a large scaled preparation.

Another object of the present invention is to produce L-homophenylalanine with a high yield. According to the present invention, L-hmophenylalanine can easily precipitate from the solution under the reaction conditions, thereby the conversion from 2-oxo-4-phenylbutanoic acid to L-homophenylalanine is driven in a direction favoring L-homophenylalanine production, resulting in a yield of over 95%.

A further object of the present invention is to produce L-homophenylalanine with a high enantiomeric excess of over 99% so that further purification and resolution become unnecessary.

In general, the present invention comprises the step of reacting 2-oxo-4-phenylbutyric acid with L-glutamic acid in the presence of tyrosine aminotransferase to produce L-homophenylalanine and L-ketoglutamic acid.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Abbreviations:

Glu: glutamic acid;
Tyr: tyrosine;
Phe: phenylalanine;
Asp: aspartic acid;
Met: methionine;
Leu: leucine;
His: histidine;
Val: valine;
Lys: lysine;
Ala: alanine;
Gly: glycine;
Thr: threonine;
Ile: isoleucine;
Ser: serine
THF: tetrahydrofuran;
ACN: acetonitrile;
TFA: trifluoroacetic acid.

Figure 1:
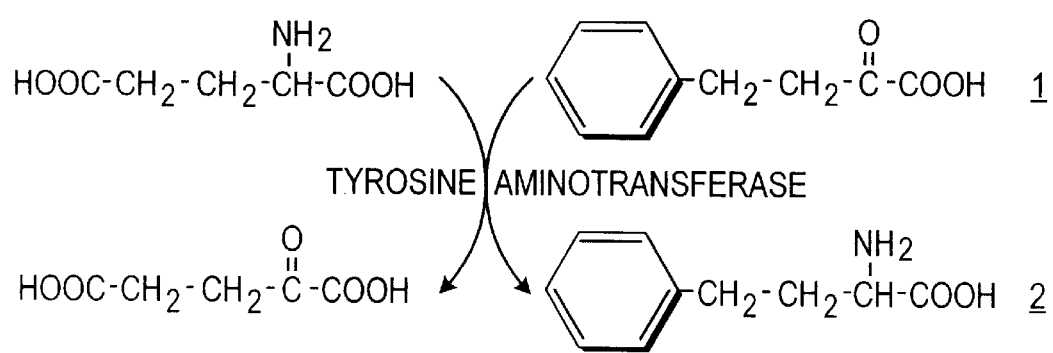
FIG. 1 is a schematic showing of the transfer of amino group reaction catalyzed by tyrosine aminotransferase.
Figure 2:
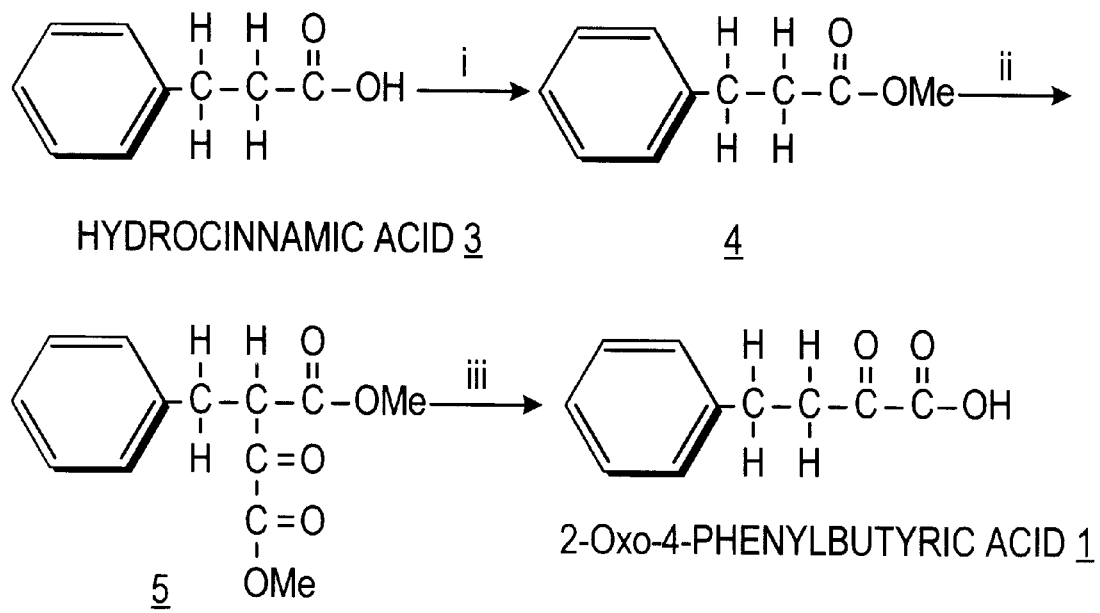
FIG. 2 is a schematic showing of 2-oxo-4-phenylbutyric acid synthesis.

Referring now to FIG. 1, a tyrosine aminotransferase-catalyzed amino transfer from glutamic acid to compound 1 (2-oxo-4-phenylbutyric acid) to produce compound 2 (homophenylalanine) is schematically shown. While compound 1 may be produced by any suitable method known to a person of ordinary skill in the art, the production of compound 1 from compound 3 (hydrocinnamic acid) shown schematically in FIG. 2 is preferred.

Synthesis of 2-oxo-4-phenylbutyric acid: As shown in FIG. 2, 1.5 g (10 mmol) of hydrocinnamic acid is dissolved in 25 ml of dry MeOH, followed by addition of 2 drops of concentrated $H_2SO_4$. The clear solution is heated to reflux for 8 hours and the resulting solution is concentrated in vacuum. The concentrate is then diluted with EtOAc, washed with saturated NaHCO₃, and dried over MgSO₄. The resulting solution is then filtered and concentrated in vacuum to yield about 1.62 g (99%) of compound 4 (FIG. 2), a light yellow liquid, having the following physical properties:

$^1$H NMR (400 MHz, CDCl₃) δ2.64(t, J=7.6 Hz, 2H, CH₂C(O)), 2.96 (t, J=7.6 Hz, 2H, CH₂Ph), 3.66 (s, 3H. OCH₃), 7.15–7.35 (m, 5H, ArH).

$^{13}$C NMR (100 MHz, CDCl₃) δ30.8, 35.6, 51.4, 126.2, 128.2, 128.4, 140.4, 173.2.

1.64 g (10 mmol) of compound 4 is then mixed with 590 mg (11 mmol) of sodium methoxide dissolved in 35 ml of tetrahydrofuran (THF). Then 1.3 g (11 mmol) of dimethyl oxalate is added to the mixture and the solution is stirred at 40° C. for 6 hours. After cooling to the room temperature (about 25° C.), 7 ml of 3N HCl is added to the cooled solution. The upper layer of the resulting solution is separated and washed with saturated NaHCO₃, dried over MgSO₄, then filtered and concentrated in vacuum to yield compound 5 (FIG. 2), which is an oil. 10 ml of 7N HCl is then added to the oil compound 5 and the mixture is refluxed for 6 hours at 100° C. The resulting solution is cooled at 4° C. and filtered to collect 1.57 g of precipitates (88% of compound 4). The precipitates so collected is compound 1 (FIG. 2), 2-oxo-4-phenylbutyric acid, having the following physical properties:

$^1$H NMR (400 MHz, CDCl₃): δ2.97(t, J=7.6 Hz, 2H, CH₂C(O)), 3.25 (t, J=7.4 Hz, 2H, CH₂Ph), 7.10–7.30 (m, 5H. pH).

$^{13}$C NMR (100 MHz, CDCl₃) d 28.9, 39.4, 126.5, 128.3, 128.6, 139.6, 160.3, 194.7.

It is noted that any 2-oxo-4-phenylbutyric acid, whether commercially available or can be made by a person of ordinary skill in the art may be used as the starting material for producing L-homophenylalanine as described in the present application.

Production of tyrosine aminotransferase: Genetically engineered tyrosine aminotransferase is preferably produced by overexpressing the gene product in *E. coli* according to the method described by Kuramitsu et al. in *Biochem, Biophys. Res. Commu.*, 1989, 133:134, the contents of which are herein incorporated by references in their entirety. One unit of enzyme activity was defined as the activity that produces 1 μmol of product per minute. The tyrosine aminotransferase so produced generally has an enzymatic activity of about 109.8 unit/ml in the culture media, although the enzymatic activities may vary from batch to batch.

The enzymatic activities of the genetically engineered tyrosine aminotransferase as described above were tested using various amino acids as amino donors and the results are shown in Table I. Each enzyme-catalyzed reaction was carried out in a mixture (5 mL) of Tris-HCl buffer (20 mM, pH 8.5) containing the tested amino acid (0.20 mmol) and 2-oxo-4-phenylbutyric acid (0.10 mmol) and the enzyme (1 unit) at 37° C. for 5 min. The initial rate was measured by calculating the increase of homophenylalanine concentration in each reaction based on HPLC analysis.

TABLE I

The initial reaction rate and turnover rate of tyrosine aminotransferase-catalyzed reaction using 2-oxo-4-phenylbutyric acid and various amino acids as substrates.

| amino acids | initial rate | turnover rate |
|---|---|---|
| L-Tyr | 3.43 | 0.619 |
| L-Phe | 3.32 | 0.605 |
| L-Glu | 2.96 | 0.539 |
| L-Asp | 2.04 | 0.372 |
| L-Met | 1.47 | 0.268 |
| L-Leu | 0.58 | 0.106 |
| L-His | 0.49 | 0.089 |
| L-Val | 0.32 | 0.058 |
| L-Lys | 0.25 | 0.046 |
| L-Ala | 0.23 | 0.042 |
| L-Gly | 0.15 | 0.027 |
| L-Thr | 0.05 | 0.009 |
| L-Ile | 0.03 | 0.005 |
| L-Ser | 0.01 | 0.002 |

As noted in Table I, L-Glu, L-Phe and L-Tyr are the most favorable amino donors having the turnover rates of 0.54, 0.61 and 0.62 mM/min.unit, respectively, for the enzyme-catalyzed reactions.

It is understood that any commercially produced genetically engineered tyrosine aminotransferases are equally applicable for the purpose of the present invention. Although genetically engineered tyrosine aminotransferase is preferred, non-genetically engineered enzymes may also be used.

Synthesis of L-homophenylalanine: The synthesis is conducted preferably in a reaction mixture (5 ml) containing Tris-HCl buffer (50 mM, pH 8.5), compound 1 (10 mmole, the final concentration of compound 1 is about 2 M), L-Glu (10 mM), pyridoxal 5-phosphate (20 mM) at 37° C. The reaction is initiated by adding the tyrosine aminotransferase (5 units) to the reaction solution and monitored by HPLC.

Figure 3:
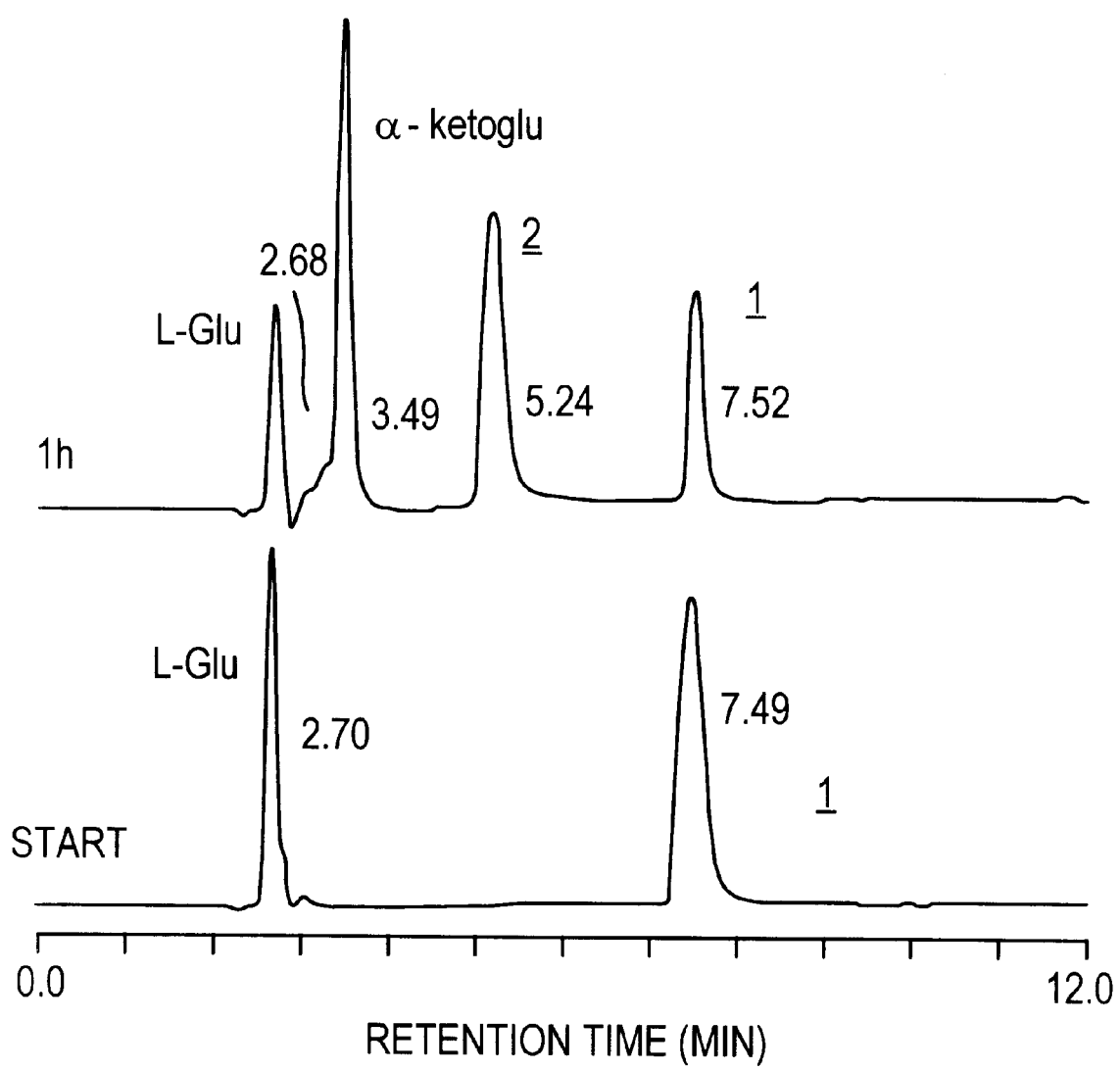
FIG. 3 is a HPLC graph, showing the separation of the four components in the tyrosine aminotransferase-catalyzed reaction.

FIG. 3 shows a typical analysis of the components in the reaction mixture. The HPLC chromatography is preferably conducted under the following conditions: column, 5C18; flow rate, 1 ml/min; gradient elution from an initial solution of 10% of eluent B+90% of eluent A to a final solution of 100% of eluent B in 20 minutes, wherein eluent A contains 5% ACN in 0.1% TFA and eluent B contains 95% ACN in 0.1% TFA; detector UV 214 nm. Initially, only peaks representing the starting materials L-glutamic acid having a retention time of 2.70 min and compound 1 having a retention time of 7.49 min appear in the HPLC graph as shown in the lower panel of FIG. 3. After adding the tyrosine aminotransferase, the areas of peaks corresponding to compound 1 and glutamic acid are decreased gradually, whereas areas of peaks corresponding to compound 2 having a retention time of 5.24 min and α-ketoglutamic acid having a retention time of 3.49 min are increased, as shown in the upper panel of FIG. 3. When the area of the peak representing compound 1 is reduced to one-fifth of the initial peak area, white precipitates appear in the reaction solution, while the peak area of compound 2 becomes stable and stays constant until the peak areas of compound 1 and glutamic acid are reduced to about baseline. This reaction profile indicates that compound 2 is practically insoluble in the reaction solution so that it precipitates before the enzymatic reaction reaches an equilibrium. Thus, the reaction is driven towards the synthesis of compound 2 to its completion, although the equilibrium constants for such reactions, as shown in Table II, suggest otherwise opposite results.

TABLE II

The equilibrium constants of tyrosine aminotransferase catalyzed reaction using 2-oxo-4-phenybutyric acid and various amino acids as substrates.

| Amino acids | Equilibrium Constant ($K_{eq}$) |
|---|---|
| L-Tyr | 0.727 |
| L-Phe | 0.466 |
| L-Glu | 0.345 |
| L-Asp | 0.187 |

For a large scaled preparation, compound 1 (100 mmol, 17.9 g), L-Glu (150 mM, 22.0 g), pyridoxal 5-phosphate (20 mM), and tyrosine aminotransferase (25 U) in Tris-HCl buffer (50 mM, pH 8.5, 50 mL) are mixed and the reaction is carried out at 37° C. for 2 hours. Under such condition, the concentration of compound 1 is about 2M. The L-homophenylalanine precipitates are collected by filtration and washed with cold water and dried in vacuum to yield about 16.71 gram of compound 2 (yield of about 95%) without further purification. Compound 2 (L-homophenylalanine) so produced has a melting point of >300° C. and is $[\alpha]^{25}_D$ +45.2° (c 1, 3N HCl).

Thus, the above described genetically engineered tyrosine aminotransferase permits the concentration of 2-oxo-4-phenylbutyric acid to go as high as about 2 M in preparation of L-homophenylalanine. Such use of a high concentration of the substrate in the present enzymatical reaction significantly reduces production cost.

Figure 4:
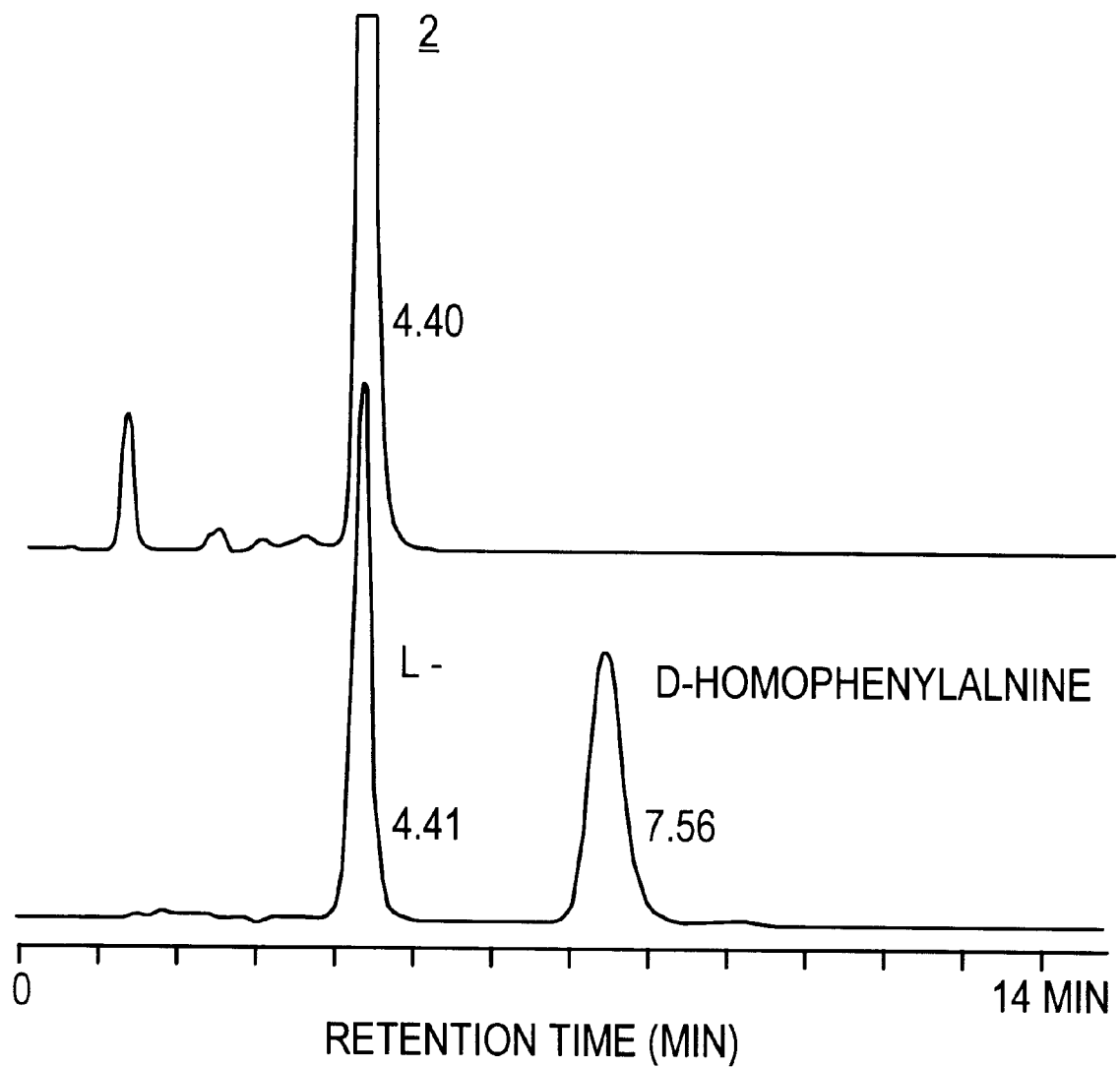
FIG. 4 is a HPLC graph, showing a measurement of the enantiomeric excess of the enzymatically synthesized L-homophenylalanine using Chiral T column.

The enantiomeric excess of compound 2 is determined using a chiral T column that shows an enantiomeric excess of over 99%. The chromatography is preferably carried out under the following conditions: column, Chiral T (from ASTEC USA); flow rate, 1 ml/min; eluents: EtOH/$H_2O$= 50/50 (v/v); and detector UV 214 nm. As shown in the lower panel of FIG. 4, racemic homophenylalanines can be separated into two peaks representing L-homophenylalanine having a retention time of 4.41 min and D-homophenylalanine having a retention time of 7.56 min. The synthetic L-homophenylalanine (compound 2) having a retention time of 4.40 min is shown in the upper panel of FIG. 4, where no D-antipode can be observed.

The genetically engineered tyrosine-aminotransferase has a broad substrate specificity so that a variety of amino acids other than glutamic acid can also be used as amino donors for the synthesis of L-homophenylalanine as described above.

The invention is not limited by the embodiments described above which are presented as examples only but can be modified in various ways within the scope of protection defined by the appended patent claims.

We claim:

1. A process for producing L-homophenylalanine, comprising the step of reacting 2-oxo-4-phenylbutyric acid with L-glutamic acid in the presence of tyrosine aminotransferase in a reaction solution to produce L-homophenylalanine and L-ketoglutamic acid such that L-homophenylalanine precipitates from said reaction solution and wherein said precipitation drives said reaction substantially to completion.

2. The process of claim 1, wherein said tyrosine aminotransferase is prepared through recombinant DNA expression.

3. The process of claim 1, wherein said tyrosine aminotransferase has an activity of about 109.8 unit/ml.

4. The process of claim 1, wherein about 95% of said L-homophenylalanine precipitates from said reaction solution.

5. The process of claim 1, wherein said L-homophenylalanine has an enatiomeric excess of over 99%.

6. The process of claim 1, wherein said 2-oxo-4-phenylbutyric acid is at a concentration of more than 0.2M.

7. The process of claim 4, further comprising the step of collecting said precipitate by filtration.

8. The process of claim 7, further comprising the step of washing said precipitate with water.

9. The process of claim 8, further comprising the step of drying said precipitate in vacuum.

10. A process for producing L-homophenylalanine, comprising the step of reacting 2-oxo-4-phenylbutyric acid with a L-amino acid in the presence of tyrosine aminotransferase in a reaction solution to produce L-homophenylalanine such that L-homophenylalanine precipitates from said reaction solution and wherein said precipitation drives said reaction substantially to completion.

11. The process of claim 10, wherein said tyrosine aminotransferase is prepared through recombinant DNA expression.

12. The process of claim 10, wherein said tyrosine aminotransferase has an activity of about 109.8 unit/ml.

13. The process of claim 10, wherein about 95% of said L-homophenylalanine precipitates from said reaction solution.

14. The process of claim 10, wherein said L-homophenylalanine has an enantiomeric excess of over 99%.

15. The process of claim 10, wherein said 2-oxo-4-phenylbutyric acid is at a concentration of more than 0.2M.

16. The process of claim 13, further comprising the step of collecting said precipitate by filtration.

17. The process of claim 16, further comprising the step of washing said precipitate with water.

18. The process of claim 17, further comprising the step of drying said precipitate in vacuum.

19. The process of claim 1, wherein the concentration of said 2-oxo-4-phenylbutyric acid is about 2M.

20. The process of claim 10, wherein the concentration of said 2-oxy-4-phenylbutyric acid is about 2M.

* * * * *